United States Patent
Weinans et al.

(10) Patent No.: US 12,144,736 B2
(45) Date of Patent: Nov. 19, 2024

(54) ACETABULAR IMPLANT AND METHOD FOR DEFORMING THIS IMPLANT

(71) Applicants: Common Sense Engineering and Consult B.V., Geel (BE); UMC Utrecht Holding B.V., Utrecht (NL)

(72) Inventors: Hermannus Hendricus Weinans, Utrecht (NL); Peter Mercelis, Geel (BE)

(73) Assignees: Common Sense Engineering and Consult B.V., Geel (BE); UMC Utrecht Holding B.V., Utrecht (NL)

(*) Notice: Subject to any disclaimer, the term of this patent is extended or adjusted under 35 U.S.C. 154(b) by 0 days.

(21) Appl. No.: 17/525,402

(22) Filed: Nov. 12, 2021

(65) Prior Publication Data
US 2022/0168110 A1    Jun. 2, 2022

(30) Foreign Application Priority Data
Nov. 12, 2020  (BE) .................................. 2020/5810

(51) Int. Cl.
*A61F 2/34*    (2006.01)
*A61F 2/30*    (2006.01)
*A61F 2/36*    (2006.01)

(52) U.S. Cl.
CPC ............ *A61F 2/34* (2013.01); *A61F 2/30767* (2013.01); *A61F 2/3094* (2013.01); *A61F 2/3662* (2013.01); *A61F 2002/30011* (2013.01); *A61F 2002/30968* (2013.01); *A61F 2310/00023* (2013.01); *A61F 2310/00131* (2013.01)

(58) Field of Classification Search
CPC ...... A61F 2/34; A61F 2/30767; A61F 2/3094; A61F 2/3662; A61F 2002/30011; A61F 2002/30968; A61F 2/30942; A61F 2002/30006; A61F 2002/30014; A61F 2002/30072; A61F 2002/3092; A61F 2002/30952; A61F 2002/30957; A61F 2002/30971; A61F 2002/30985
See application file for complete search history.

(56) References Cited

U.S. PATENT DOCUMENTS

| | | | |
|---|---|---|---|
| 5,030,233 A | | 7/1991 | Ducheyne |
| 6,066,176 A | * | 5/2000 | Oshida ................ A61F 2/30907 623/23.62 |
| 7,208,222 B2 | * | 4/2007 | Rolfe ...................... A61F 2/442 428/137 |
| 9,498,339 B2 | | 11/2016 | Berend et al. |

(Continued)

FOREIGN PATENT DOCUMENTS

| EP | 0145339 A2 | 6/1985 |
|---|---|---|
| WO | 2008015290 A1 | 2/2008 |
| WO | 2008106192 A2 | 9/2008 |

*Primary Examiner* — Ariana Zimbouski
*Assistant Examiner* — Yasniary De La Caridad Morales
(74) *Attorney, Agent, or Firm* — FISHERBROYLES, LLP

(57) ABSTRACT

Acetabular implant and method for its manufacture, wherein the implant has a bone side with a contact surface to be fixed against the bone of the hip socket. A plastically deformable zone with an open porous structure connects to the contact surface, the zone being formed by a three-dimensional structure composed of strut elements with opposite ends, wherein these strut elements are connected at their ends in nodes. The zone is made of a material having an elongation at break of at least 15%.

19 Claims, 3 Drawing Sheets

(56) References Cited

U.S. PATENT DOCUMENTS

| | | | |
|---|---|---|---|
| 2009/0234459 A1* | 9/2009 | Sporring | A61L 27/446 623/18.11 |
| 2012/0150310 A1* | 6/2012 | Taylor | A61F 2/4609 623/22.21 |
| 2013/0056912 A1* | 3/2013 | O'Neill | C23C 4/02 264/497 |
| 2013/0158672 A1* | 6/2013 | Hunt | A61F 2/30767 623/23.5 |
| 2014/0265062 A1* | 9/2014 | Sanchez | A61F 2/34 264/642 |
| 2015/0012109 A1 | 1/2015 | Moreau et al. | |
| 2019/0046322 A1* | 2/2019 | Moore | A61F 2/3859 |
| 2022/0183847 A1* | 6/2022 | Tepic | A61F 2/34 |

\* cited by examiner

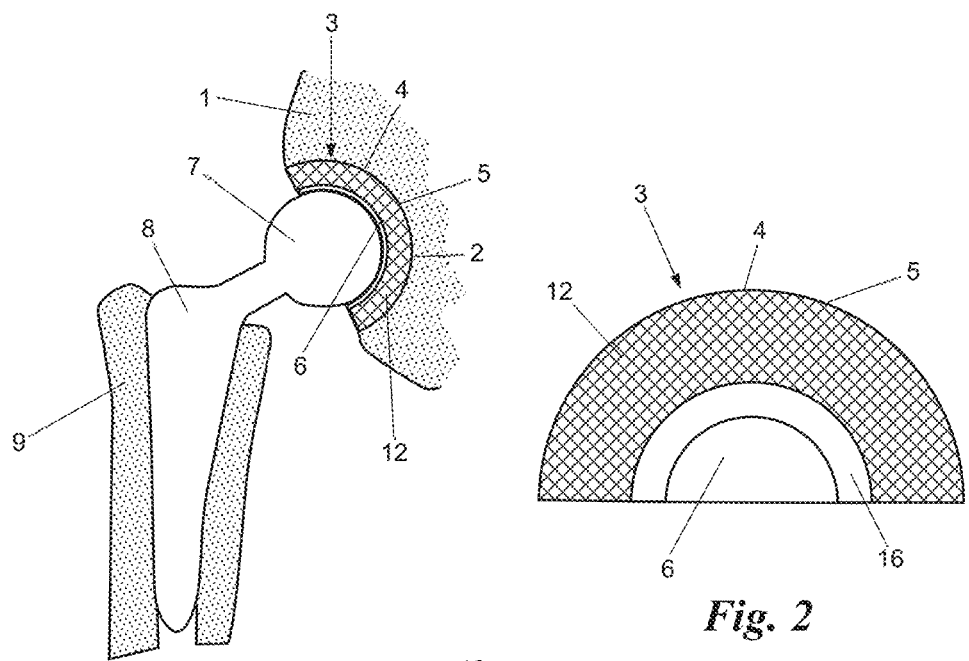
Fig. 1
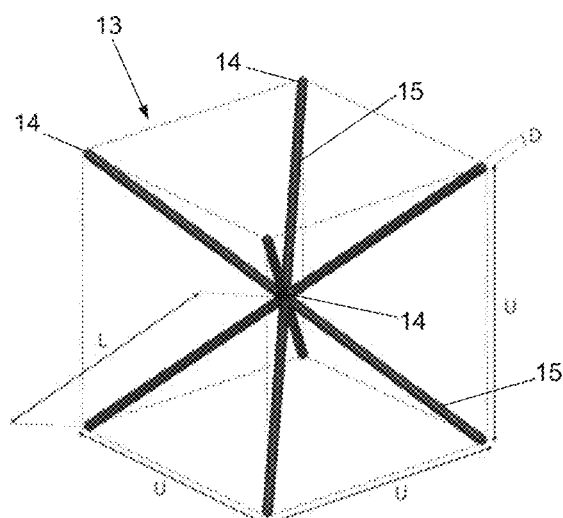
Fig. 2
Fig. 3
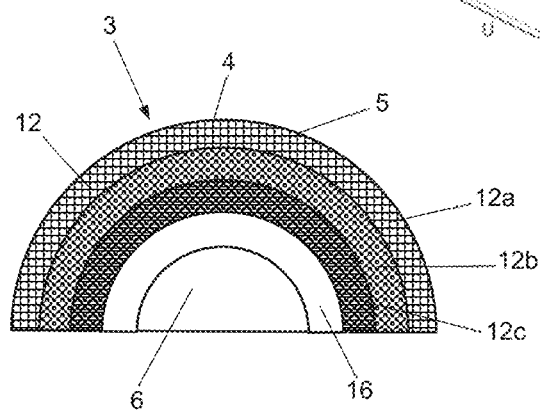
Fig. 4

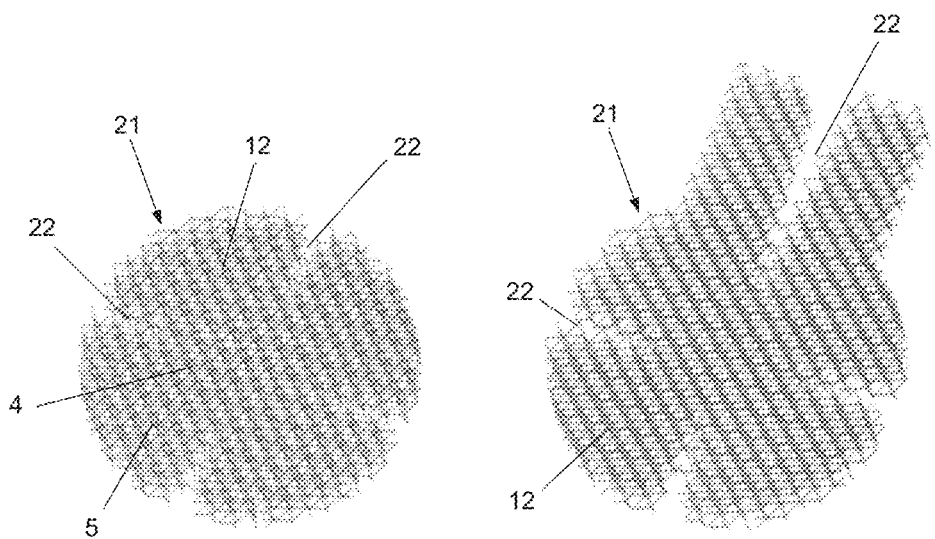
*Fig. 11*   *Fig. 12*
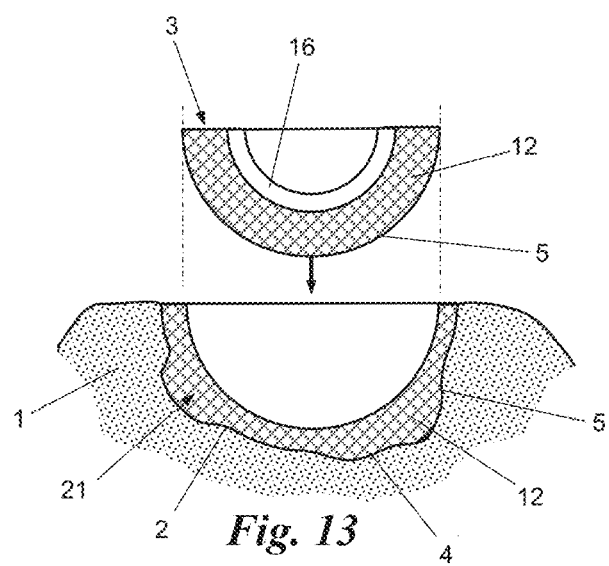
*Fig. 13*

ACETABULAR IMPLANT AND METHOD FOR DEFORMING THIS IMPLANT

The invention relates to an acetabular implant to be inserted into a hip socket. This implant has a bone side with a contact surface to be fixed against the bone of the hip socket. A plastically deformable zone with an open porous structure connects to this contact surface. This zone is formed by a three-dimensional structure made up of strut elements with opposite ends, these strut elements being connected at their ends in nodes. At least three strut elements are connected in each node. The plastically deformable zone has a yield strength comprised between a minimum value and a maximum value, wherein this minimum value corresponds to a maximum load of said zone in vivo, after attaching the implant to the bone surface in the body.

Acetabular implants which are currently in use include standard size implants on the one hand, and custom-made patient-specific implants on the other hand. The implants are usually secured in the hip socket with bone cement or screws. When the hip socket is formed of poor quality bone or when bone defects are present, additional flanges may be provided to the implant to anchor the latter to the hip bone.

Documents EP 0145339, U.S. Pat. No. 5,030,233 and WO 2008/015290 describe implants which are only very slightly adaptable to the shape of the cavity of the hip socket and thus can undergo only minor deformations thanks to the presence of a thin deformable layer. U.S. Pat. No. 9,498,339 describes such an implant which additionally requires the use of a bone cement to perpetuate deformations of the implant.

The use of standard-sized acetabular implants is often unsatisfactory in the presence of bone defects in the hip socket or when the bone of the hip socket is of insufficient quality. Manufacturing a patient-specific acetabular implant is quite laborious and relatively expensive for a patient. It is generally observed that the long-term stability of acetabular implants is often insufficient, with inadequate bone ingrowth in the implant or sometimes bone resorption occurring.

The invention aims to propose an acetabular implant which makes it possible to fill bone defects in the hip socket in a simple manner, while achieving a stable anchoring of the implant in the hip socket, even with poor bone quality or in the presence of very large bone defects. In addition, the invention aims to stimulate bone growth in the implant and does not normally require the use of screws or cement to secure the implant in the hip socket. In addition, the invention provides a patient-specific acetabular implant.

To this end, said maximum value for the yield strength of the plastically deformable zone corresponds to a medically justifiable maximum load applied to said bone surface when placing the implant on the bone.

Practically, said zone is made of a material exhibiting an elongation at break of at least 15%, and preferably at least 20%.

Advantageously, the minimum value of the yield strength of said plastically deformable zone is 0.1 MPa. The maximum value of the yield strength of said zone is, for example, 1 MPa and, preferably, 0.5 MPa.

According to a preferred embodiment of the implant according to the invention, the elastic modulus of said zone is comprised between 0.02 MPa and 0.08 MPa.

According to a major embodiment of the implant according to the invention, the theoretical porosity of said zone is comprised between 80% and 99.5%. In an interesting manner, it is comprised between 90% and 99.5%.

Preferably, at least said plastically deformable zone of the implant is made of titanium, in particular of commercial, pure titanium. According to an alternative embodiment, this zone may also be made of other materials such as tantalum or it may be composed of a combination of different materials, such as, for example, pure titanium and tantalum.

According to an interesting embodiment of the implant according to the invention, said strut elements forming said three-dimensional structure have a length-to-thickness ratio comprised between 10 and 25.

The length of these strut elements is comprised, for example, between 3 mm and 10 mm. Further, the strut elements preferably have a diameter between 100 µm and 400 µm. Preferably, however, the length of the strut elements is greater than 3 mm and less than 5 mm, while their thickness is between 100 µm and 300 µm.

According to a particularly interesting embodiment of the implant according to the invention, said three-dimensional structure is composed of body centered cubic unit cells with lattice points coinciding with said nodes.

According to a major embodiment of the implant according to the invention, said contact surface extends according to a substantially half sphere on said bone side, while opposite said bone side is provided a socket for receiving a hip head. Optionally, a coating is provided between the hip head and said socket of the implant. In this implant, at least one parameter of said plastically deformable zone increases from said bone side to said socket, said parameter being selected from the set of yield strength, elastic modulus, length-to-thickness ratio of the strut elements and/or theoretical density.

Said plastically deformable zone occupies, for example, at least 20% of the total volume of the acetabular implant. According to other interesting embodiments, said volume of the plastically deformable zone constitutes at least 40% or possibly at least 60% of the total volume of the acetabular implant.

The invention also relates to a method for manufacturing a patient-specific acetabular implant to be placed in a patient's hip socket. According to this method:
- a pressing mold is manufactured whose geometry corresponds to the geometry of the hip socket,
- an acetabular implant is selected which is oversized for the patient's hip socket, said oversized acetabular implant having a bone side with a contact surface to be attached to the bone of the hip socket and having a plastically deformable zone with an open porous structure that connects to said contact surface, and
- said oversized acetabular implant is pressed into the pressing mold with said bone side, thus deforming said plastically deformable zone.

Other particularities and advantages of the invention will become clear from the following description of some specific embodiments of the implant and method according to the invention. This description is given by way of example only and does not limit the scope of the protection claimed; the reference numerals used below refer to the figures appended hereto.

FIG. 1 is a schematic longitudinal section of a hip socket with an acetabular implant in which there is a hip head connected to the top of a femur by a hip stem.

FIG. 2 is a schematic cross-section of an acetabular implant according to the invention.

FIG. 3 is a schematic view in perspective of a cubic, spatially centered unit cell of strut elements for a three-dimensional structure of an acetabular implant according to an interesting embodiment of the invention.

FIG. 4 is a schematic cross section of an acetabular implant according to a preferred embodiment of the invention.

FIG. 11 is a schematic view in perspective of an implant according to the invention, formed by a circular disk from a three-dimensional lattice structure.

FIG. 12 is a similar view in perspective of an implant like that in FIG. 11 forming a disk with a rather elongated shape.

FIG. 13 is a schematic cross-section of a hip socket in which the implant from FIG. 11 has been placed.

In the various figures, the same reference numerals refer to the same or analogous elements.

Figure 5:
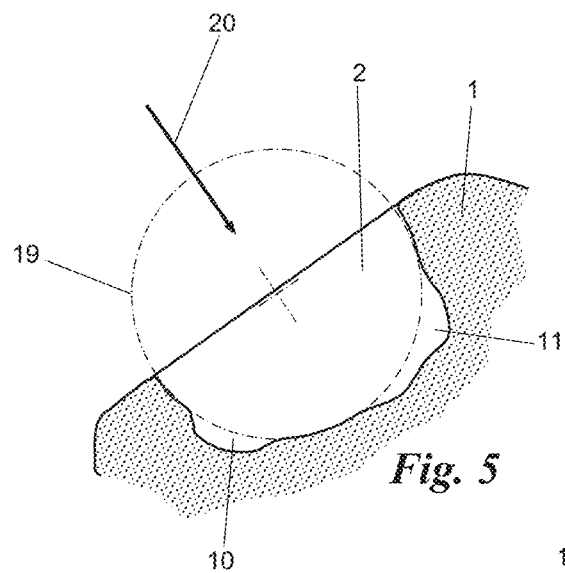
FIG. 5 is a schematic cross section of a hip socket with bone defects.

The invention relates generally to an acetabular implant to be placed in a patient's hip socket. Such an acetabular implant normally has the shape of a hemispherical sphere whose external spherical surface is to be fixed against the inner surface of the hip socket. On the side of the implant opposite this spherical surface, a socket is provided in the implant with a surface that is usually also shaped like a semi-sphere and into which a hip head should fit, as shown in FIG. 1.

FIG. 1 schematically represents a part of a hip 1 with a hip socket 2, also called acetabulum, in which an acetabular implant 3 is fixed. This implant 3 has a bone side 4 on which a contact surface 5 extends describing practically a semi-sphere and which is fixed to the bone of the hip socket 2. Opposite the bone side 4, the implant 3 has a socket 6 so as to receive a spherical hip head 7. The latter is connected to the top of the femur 9 via a hip stem 8.

FIG. 1 shows a hip socket 2 which substantially has the shape of a semi-sphere without any bone defects. However, the invention relates to an acetabular implant and a method that not only allow the implant to be placed in a hip socket 2 where there are virtually no relevant bone defects, but also in a hip socket 2 that has significant bone defects 10 and 11, as is schematically represented in the hip socket 2 of FIG. 5.

The acetabular implant according to the invention is a porous, deformable implant 3 which is manufactured, for example, by means of a 3D printing technique, in particular an additive manufacturing technique, such as, for example, selective laser melting (SLM). At least part of the implant is thus plastically deformable and is preferably manufactured from titanium or possibly from tantalum. The acetabular implant is designed in such a way that it becomes possible to fill unwanted cavities or defects in bone tissue.

Thus, for the acetabular implant, an implant is selected that is oversized in relation to the cavity of the hip socket into which it is to be inserted, so that it is sufficiently large to fit snugly on the hip socket after having been compressed and plastically deformed upon insertion into the hip socket. To this end, the structure and porosity of the implant 3 according to the invention are selected such that at least part of it deforms under compression. When the implant 3 is thus placed in the hip socket 2 by a surgeon, the surgeon will exert a compressive force on the implant 3 such that it is compressed in the hip socket and plastically deformed. As a result of this deformation, the shape of the bone side 4 of the implant 3 adapts to the geometry of the hip socket 2 and thus accurately matches the contours of the bone tissue in the hip socket 2. In the design of the acetabular implant 3 according to the invention, it is preferably made sure that it has a positive Poisson's ratio. The latter ensures that the implant 3 expands in transverse directions with respect to the compression force exerted by the surgeon when inserting the implant 3 into the hip socket 2. Thus, the implant 3 seemingly flows into the bone cavities or bone defects present in the hip socket as a result of the force exerted by the surgeon, thereby achieving a good anchorage of the implant 3 in the bone tissue.

In particular, in the presence of bone defects in the acetabulum 2, an acetabular implant 3 can be designed on the basis of the above concept which is larger in size than the semi-sphere of the acetabular cavity. When such an oversized porous and plastically deformable implant 3 is inserted into the hip socket 2 under compression, the porous structure of the bone side 4 of the implant 3 will plastically deform and adapt almost exactly to the dimensions of the acetabulum 2, as a result of which the implant 3 will clamp itself into the cavity of the hip socket 2 and penetrate into bone defects present.

Even if no bone defects are present, the acetabular implant according to the invention can clamp itself in the acetabular semi-sphere because, as a result of the compressive force exerted on the implant 3 during its placement, the implant 3 will expand in directions transverse to this compressive force.

By an oversized acetabular implant 3 is meant an acetabular implant 3 whose diameter is greater than the diameter of a spherical surface 19 describing the cavity of the hip socket 2 or, in other words, whose diameter is larger than the diameter of the largest sphere 19 tangent to the cavity of the hip socket 2 internally, as is schematically represented in FIG. 5.

According to a preferred embodiment of the acetabular implant according to the invention, it has a plastically deformable zone 12 with an open, porous structure that opens onto the contact surface 5 of the bone side 4. This deformable zone 12 is preferably formed by a three-dimensional structure composed of strut elements connected to each other at their ends in nodes, such that at least three strut elements are connected to each other in each node. The strut elements are formed, for example, by elongated rods.

More specifically, the deformable zone 12 is formed by a three-dimensional lattice structure composed of interconnected unit cells of said strut elements. FIG. 3 thus shows a body-centered cubic unit cell 13 by way of example. The lattice points of this unit cell coincide with said nodes 14 in between which the strut elements 15 extend.

The body-centered cubic unit cell shown in FIG. 3 has ribs with a length U, while the strut elements 15 of this unit cell have a length l, thus holding that $l=(\sqrt{3}\cdot U)/2$. These strut elements 15 have a circular cross-section with a thickness d corresponding to their diameter.

In addition to or as an alternative to this body-centered cubic unit cell, it is also possible to employ a three-dimensional lattice structure composed of other unit cells, such as, for example, a diamond unit cell or a rhombic dodecahedron unit cell in the deformable zone 12. However, it was found that for an implant made of a lattice structure of body-centered cubic unit cells, the force required to insert it into the hip socket and to cause its plastically deformable zone 12 to flow into bone defects is easily controllable by a surgeon. Thus, this allows a surgeon to place the implant in the hip socket with a force application and according to a method for placing acetabular implants according to the present state of the art, with which the surgeon is already familiar.

The plastically deformable zone 12 is not necessarily composed of a repetitive repetition of unit cells. For example, the structure forming the zone 12 may be formed by a structure defined, in general, by nodes between which strut elements extend in random directions. More specifically, the structure of the plastically deformable zone should not necessarily have a regular geometry.

According to the invention, the structure of said porous and plastically deformable zone 12 is thus selected such that this zone has a yield strength between a minimum value $\sigma_{min}$ and a maximum value $\sigma_{max}$. This minimum value $\sigma_{min}$ thereby corresponds to a maximum load of said zone in vivo, after fixing the implant to the bone surface. Thus, this minimum value $\sigma_{min}$ corresponds to the maximum stress exerted on the zone 12 of the implant 3 after it has been placed in the body of a patient during normal activities of said patient.

By the yield strength of said zone 12 is understood the yield strength of the structure of which this zone consists. Thus, the yield strength of the zone 12 corresponds to the compressive stress at which the structure of the zone 12 changes from elastic deformation to plastic deformation. Consequently, the yield strength of the zone 12 is different from the yield strength of the material from which the structure itself is made.

The maximum value for this yield strength of the zone 12 corresponds to a medically justifiable maximum load that can be applied to the bone surface of the hip socket 2 when the implant 3 is placed against its bone. More specifically, this medically justifiable maximum load refers to the maximum force that a surgeon may apply to the implant when placing it in the hip socket 2 without causing any damage to the hip. The implant 3 is hereby inserted into the hip socket 2, for example by hammering, in a manner known to the professional. Acetabular implants are currently being placed, for example, in a hip socket by applying impact forces averaging 16.8 kN to the implant with a peak load of, for example, approximately 27.5 kN. Thus, said medically justifiable maximum load corresponds to a peak load of, for example, substantially 30 kN applied to the implant.

According to a preferred embodiment of the invention, the minimum value of the yield strength of the plastically deformable zone 12 of the implant is 0.1 MPa.

The maximum value of the yield strength of this zone 12, according to the invention, is 1 MPa and preferably 0.5 MPa.

In order to ensure that the implant 3 can deform sufficiently, without any fractures occurring in the structure of said plastically deformable zone 12, said zone 12 is made of a material that has an elongation at break of at least 15%. Preferably, said elongation at break is at least 20%. With such an elongation at break, said strut elements 15 can undergo a sufficient plastic deformation to allow the implant 3 to fit substantially snugly into the hip socket 2 as a result of the plastic deformation of the zone 12 and its flow into the bone defects. Commercially pure titanium is thus satisfactory and has, for example, an elongation at break which is usually comprised between 20% and 30%. Another material which is also suitable for forming said structure of the plastically deformable zone 12 is, for example, tantalum.

A commonly used titanium alloy for medical implants such as Ti-6Al-4V has insufficient plasticity and an elongation at break that is less than 15% and therefore not suitable to form the strut elements of said plastically deformable zone 12.

Further, the elastic modulus of the plastically deformable zone 12 before it is plastically deformed, according to the invention, is advantageously comprised between 0.02 MPa and 0.08 MPa. Such a choice for the elastic modulus ensures that, after plastic deformation of the implant, by inserting the acetabular implant 3 into the hip socket 2, an elastic deformation is still present. The elastic tension thus exerted by said contact surface 5 of the implant 3 on the surface of the bone of the hip socket 2 ensures, on the one hand, that the implant is firmly clamped in the hip socket 2 and, on the other hand, this tension exerted on the bone of the hip socket 2 will stimulate bone growth. Thanks to this bone growth, the accreted bone will penetrate via the contact surface 5 into the pores of said zone 12 in such a way that the implant 3 is firmly anchored in the hip socket 2 also in the long term.

When the acetabular implant 3 is deformed while being inserted into the hip socket 2, the rigidity of said plastically deformable zone 12 will increase the further it is deformed. At the same time, the yield strength of said plastically deformable zone 12 for obtaining additional plastic deformation will also increase as the structure has already been plastically deformed to a certain extent.

In order to allow for deformation of the plastically deformable zone 12 and to ensure that bone growth can occur in the implant, the plastically deformable zone has a theoretical porosity before deformation that is between 80% and 99.5%. Such porosity ensures, for example, that there is sufficient space between said strut elements in order to allow them to plastically deform, for example by bending.

The theoretical porosity of a porous structure is expressed here as follows: ' theoretical porosity=100−theoretical density', wherein the theoretical density of this porous structure is defined as the ratio of the volume of the strut elements 15 forming the structure to the total volume of the structure. For example, the volume of the strut elements 15 is determined using a CAD program in which the structure for the deformable zone 12 is designed.

Thus, the dimensions of the strut elements 15 in said three-dimensional structure of the zone 12 are selected such that they have a length-to-thickness ratio comprised between 10 and 25.

In this case, these strut elements 15 have a length which is comprised, for example, between 3 mm and 10 mm, while they have a thickness, more particularly a diameter, comprised between 100 μm and 400 μm.

For example, a suitable acetabular implant 3 has a plastically deformable zone 12 made of pure titanium (grade 1) and is composed of body-centered cubic unit cells with dimensions of 4×4×4 mm, and the strut elements 15 having a thickness of 0.2 mm. The length-to-thickness ratio of these strut elements 15 is approximately 17.3. This acetabular implant 3 is oversized in relation to the cavity of the hip socket 2, the oversize being 4 mm according to its insertion direction into the hip socket 2. Thus, the diameter of the acetabular implant is 4 mm larger than the diameter of the spherical surface 19 describing the cavity of the hip socket 2, as mentioned above and illustrated in FIG. 5.

The invention generally relates to an oversized acetabular implant whose plastically deformable zone 12, as a result of plastic deformation, is subject to a volume reduction of at least 5% when the implant is placed in the hip socket 2 as a result of the impact load thereby applied to the implant in the process. This volume reduction of the plastically deformable zone 12 may exceed 10% or even 15%.

Consequently, an oversized acetabular implant according to the invention preferably has a radius that is 1 mm larger than the radius of said spherical surface 19 describing the cavity of the hip socket 2. Preferably, the excess of this radius over said spherical surface 19 is comprised between 1 mm and 2 mm, but it may also be larger than 2 mm.

The acetabular implant 3 is preferably manufactured by applying an additional manufacturing technique, also referred to as three-dimensional printing technique, such as, for example, selective laser melting (SLM) or selective laser sintering (SLS). In this case, the implant is designed in a CAD program, for example, and then manufactured using an additional manufacturing technique.

The implant 3 shown in FIG. 2 has a contact surface 5 that extends along a semi-sphere on its bone side 4. On the side opposite the bone side 4, a socket 6 is provided for receiving the hip head 7. This socket 6 has a wall 16 that has a low plasticity and a high rigidity, such that it hardly deforms when the implant is placed in the hip cavity 2. This wall 16 may consist, for example, of a titanium alloy with high strength and high resistance to metal fatigue such as Ti6Al4V. Optionally, the inside of the socket 6 is additionally coated with plastic or a suitable metal, as is already done by professionals according to present the state of the art.

As shown in FIG. 2, said plastically deformable zone 12 is provided on the outside of the wall 16 of the socket 6, which must deform plastically when the implant 3 is placed in the hip socket 2 as described above.

The zone 12 may have a uniform structure between said wall 16 of the socket 6 and said contact surface 5, as illustrated in FIG. 2. According to another interesting embodiment of the invention, one or several parameters, such as yield strength, elastic modulus, length-to-thickness ratio of the strut elements 15 and/or theoretical density, gradually increase in the plastically deformable zone 12 according to the radial direction from the bone side 4 of the implant towards the socket 6. The acetabular implant, for example, has the lowest yield strength on said bone side 4 and the highest yield strength near said socket 6. In this manner is ensured that plastic deformation of the implant mainly occurs on the bone side 4. Consequently, the plastic zone 12 deforms preferentially on its bone side 4 when the implant is inserted into the hip socket. This offers the advantage that the material of the zone 12 on the contact surface 5 penetrates very well into any possible bone defects when the implant 3 is pressed into the hip socket 2.

According to an alternative embodiment of the invention, said plastically deformable zone 12 is composed of radially successive concentric layers 12a, 12b and 12c, as shown in FIG. 4. The yield strength, elastic modulus, the length-to-thickness ratio of the strut elements 15 and/or the theoretical density of the three-dimensional structure of the relevant layer increases as the distance between said bone side 4 and said layer increases here.

It is also possible to use different types of said unit cells in the three-dimensional structure of the zone 12. For example, one may choose to use unit cells near the contact surface 5 having a lower yield strength than unit cells located closer to the wall 16 of the socket 6.

In certain cases, it may be medically less appropriate to deform the oversized acetabular implant 3 according to the invention during its insertion into the hip socket 2. This may be the case, for example, if one wishes to limit the number of impulse loads applied when hammering the implant to insert it into the hip socket, or the magnitude of these loads.

Figure 8:
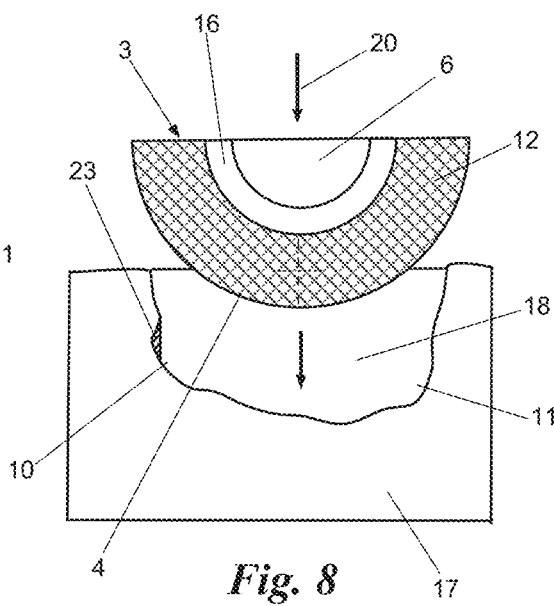
FIG. 8 is a schematic cross-section of a press mold with a recess having the geometry of a hip socket for applying the method according to the invention.
Figure 9:
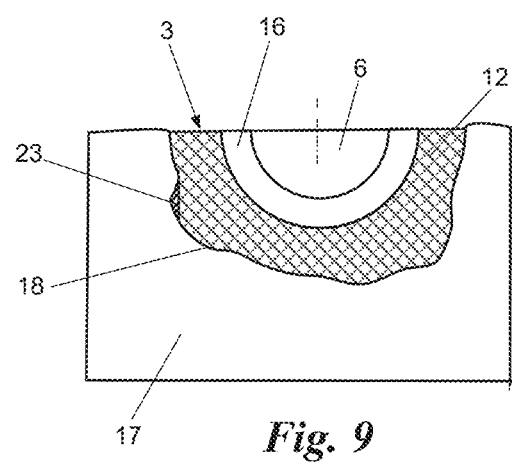
FIG. 9 is a schematic cross-section of the press mold shown in FIG. 8 after an acetabular implant has been deformed therein.

In order to achieve this, according to the invention, a press mold is manufactured whose geometry corresponds to the geometry of the hip socket 2. FIGS. 8 and 9 schematically illustrate such a press mold 17.

In order to manufacture this press mold, a CT scan is made of the hip socket 2, for example, and a digital model of the cavity of the hip socket 2 is subsequently generated from this CT scan. Based on this digital model, the press mold 17 is then manufactured in a manner known as such, for example by milling or by using an additive manufacturing technique. It is thereby ensured that the press mold has a recess 18 whose geometry corresponds to the geometry of the cavity of the hip socket 2. Thus, the recess 18 in press mold 17 also exhibits, for example, the bone defects 10 and 11.

In addition, an acetabular implant 3 is selected that is oversized for the patient's hip socket 2. As already described above, this acetabular implant 3 has a bone side 4 with a contact surface 5 that is to be fixed to the bone of the hip socket 2. This implant 3 also has a plastically deformable zone 12 with an open porous structure that connects to the contact surface 5.

Figure 7:
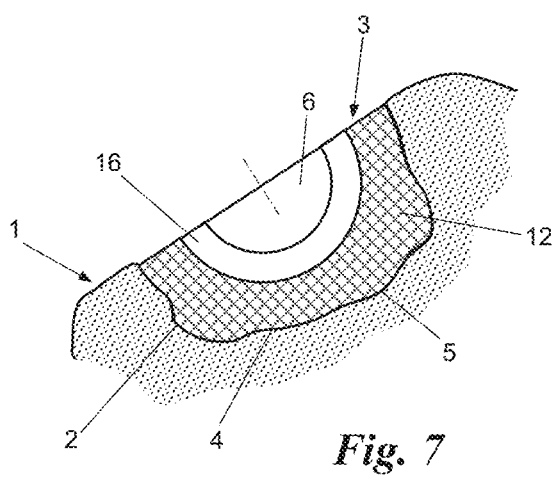
FIG. 7 is the schematic cross-section of the hip socket from FIG. 5 after the acetabular implant according to the invention has been fixed in this hip socket.
Figure 10:
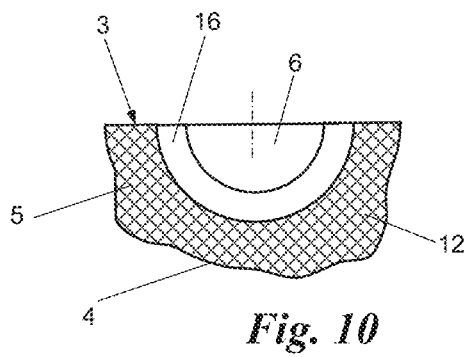
FIG. 10 represents a schematic cross section of the acetabular implant before it is placed in the hip head and after it has been deformed in the press mold from FIGS. 8 and 9.

This oversized acetabular implant 3 is pressed with the bone side 4 into the press mold, as shown in FIG. 8, so that the said plastically deformable zone 12 is deformed. The implant 3 is thus pressed into the recess 18 of the press mold 17 into a position corresponding to its planned and desired position in the cavity of the hip socket 18, as shown in FIG. 9. In this way, a patient-specific, plastically deformed acetabular implant 3 is obtained, as shown in FIG. 10. This implant 3 is then placed in the hip socket 6 so as to suitably clamp it therein, as is schematically represented in FIG. 7.

When planning the manufacture of a patient-specific acetabular implant 3, a position and orientation for this implant 3 are selected in relation to the hip socket 2. Thus, the oversized acetabular implant 3 is pressed into the press mold 17 until this position and orientation are achieved, or up to a planned deviation from this position and orientation. With the implant 3 being deformed in the press mold 17 up to said planned deviation, when this partially plastically deformed implant 3 is then placed in the hip socket 2, it will be further plastically deformed until the selected position and orientation have been achieved in the hip socket 2.

Figure 6:
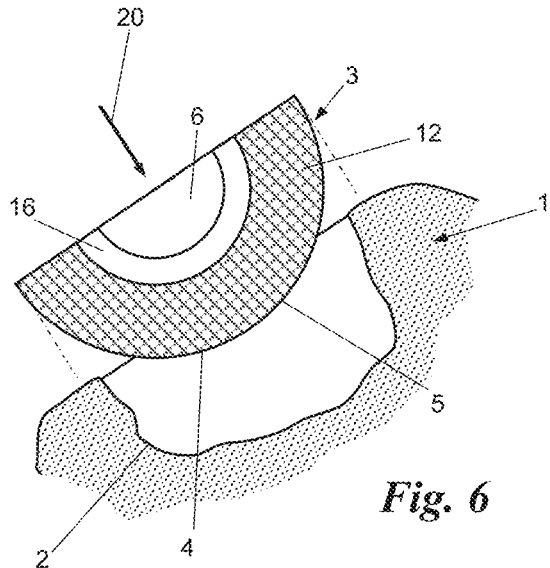
FIG. 6 represents the cross-section from FIG. 5 together with an acetabular implant according to the invention, placed in the hip socket according to an insertion direction.

Furthermore, an insertion direction is preferably also selected for placing the patient-specific acetabular implant in the hip socket 2. This direction of insertion is schematically represented by arrow 20 in FIGS. 5, 6 and 8. Thus, the oversized acetabular implant 3 is inserted according to said insertion direction 20 in the recess in the press mold 17, wherein a pressure force according to this insertion direction is applied to the implant 3 in order to deform it in the process. When selecting the insertion direction, the presence of possible undercuts may be taken into account, for example, in order to avoid them in the shape of the recess 18 of the press mold 17 or to keep them to a minimum.

When the shape of the hip socket 2 shows undercuts according to the selected input direction 20, these undercuts can be filled in the press mold 17 in order to allow an easy removal of the implant 3 from the recess 18 of the press mold 17 after it has been plastically deformed. According to an alternative method, the undercut can be digitally removed from the 3D model of the press mold before manufacturing the latter. Thus, by way of example, in FIG. 8, a part of the bone defect 10 forming an undercut has been filled up in the drilling jig 17, as indicated by the shading 23.

If an undercut has rather limited dimensions, it may be decided to just leave it in the press mold 17. In such a case, after the plastic deformation of the implant 3, upon its removal from the press mold 17, the implant 3 will be plastically deformed again. When the implant 3 is subsequently placed in the hip socket 2 according to the selected insertion direction 20, it will be subject to plastic deformation again in order to fit snugly into the cavity of the hip socket 2.

In certain cases, the plastic deformation of the oversized acetabular implant 3 in the press mold 17 ends at a planned distance, according to said insertion direction, before reaching said selected position and orientation. In this way, it can be avoided, for example, that its plastically deformable zone 12 will flow into undercuts. When the implant is subsequently placed in the hip socket 2, it is further deformed so that it is anchored in the cavity of the hip socket 2 by the presence of said undercuts into which the plastically deformable zone 12 then flows out due to its plastic deformation.

FIG. 11 shows yet another embodiment of an implant 21 according to the invention. This implant 21 is formed by a three-dimensional plastically deformable grid structure and thus consists almost entirely of a plastically deformable zone 12. The implant 21 shown in FIG. 11 forms a circular disc and is provided with V-shaped cutouts 22 extending from the circumference of the disc in a radial direction to improve the deformability of the implant. However, these cutouts 22 need not necessarily be present.

Further, this disc-shaped implant 21 also has an open porous structure formed by a three-dimensional structure made up of strut elements 15 with opposite ends, with ends being connected to each other, as represented for example in FIG. 3.

The lattice structure of this disc-shaped implant 21 is composed, for example, of cubic, spatially centered unit cells measuring 4×4×4 mm, with the cylindrical strut elements having a diameter of 0.2 mm. This implant 3 has a thickness of approximately 1 cm.

For example, the implant 21 is made of pure titanium having an elongation at break which is greater than 15% or 20%.

One of the circular surfaces of this implant 21 is a bone side 4 and thus forms a contact surface 5 to be fixed against the bone of the hip socket 2.

According to the invention, this implant 21 is placed with its contact surface 5 against the surface of the cavity of the hip socket 2 and a compressive force is thereby applied to the implant 21, such that it deforms plastically and fits almost perfectly to the hip socket 2, as shown in FIG. 13. More particularly, this implant 21 is placed in the hip socket 2 by a surgeon who, for example, by hammering, deforms it plastically and thus makes it fit into the hip socket 2.

Next, an acetabular implant 3 is placed in the cavity of the hip socket 2 against the surface of said disc-shaped implant 21 which is opposite the bone side 4 thereof. This acetabular implant 3, as described above, has a semi-spherical contact surface 5 and is undersized in relation to the cavity of the hip socket 2.

By an undersized acetabular implant 3 is thus meant an acetabular implant 3 whose diameter is smaller than the diameter of the largest sphere 19 tangent to the cavity of the hip socket 2 internally, as is schematically represented in FIG. 5.

In combination with the aforementioned disc-shaped implant 21, which has a thickness before compression of almost 1 cm, an undersized implant 6 is used, for example, whose diameter is almost 6 mm smaller than said sphere 19.

FIG. 12 shows a variant of the embodiment of the disc-shaped implant 21, wherein it has a rather elongated shape in order to be placed in a hip socket 2 with a corresponding elongated bone defect.

The invention is, of course, not limited to the embodiments of the implant 3 described above and represented in the accompanying figures, nor to the method of manufacturing an implant 3. It may be of interest, for example, in the presence of very large bone defects, to additionally provide one or more flanges to the implant for additional attachment of the implant 3 to the hip bone with screws, for example.

Furthermore, it is also possible, when designing the implant 3, to adapt the shape of said zone 12, in particular of its bone side 4, to the specific shape of a patient's hip socket 2. Hereby, it is also ensured that the implant is at least oversized in relation to the hip socket 2.

The invention claimed is:

1. An acetabular implant to be placed in a hip socket having a bone surface, the acetabular implant having a bone side with a contact surface to be fixed against the bone surface of the hip socket, wherein a plastically deformable zone with an open porous structure connects to said contact surface, said zone being formed by a three-dimensional structure composed of strut elements with opposite ends, wherein these strut elements are connected at their ends in nodes, such that at least three strut elements are connected in each node, wherein said strut elements of said zone are made of a material having an elongation at break of at least 15%, wherein said zone has a yield strength comprised between a minimum value and a maximum value, wherein said minimum value corresponds to a maximum load of said zone in vivo, after attaching the implant to the bone surface of the hip socket, and wherein said maximum value corresponds to a medically justifiable maximum load exerted on said bone surface when placing the implant against the bone of the hip socket, wherein said minimum value of the yield strength of said zone amounts to 0.1 MPa.

2. The acetabular implant according to claim 1, wherein said maximum value of the yield strength of said zone amounts to 1 MPa.

3. The acetabular implant according to claim 1, wherein the theoretical porosity of said zone is comprised between 90% and 99.5%.

4. The acetabular implant according to claim 1, wherein at least said plastically deformable zone is made of titanium, in particular commercially pure titanium, and/or tantalum.

5. The acetabular implant according to claim 1, wherein said strut elements have a tubular shape with a circular or ovoid cross-section.

6. The acetabular implant according to claim 1 wherein said strut elements have a length-to-thickness ratio between 10 and 25.

7. The acetabular implant according to claim 1, wherein said strut elements have a length between 3 mm and 10 mm.

8. The acetabular implant according to claim 1, wherein said strut elements have a diameter between 100 μm and 400 μm.

9. The acetabular implant according to claim 1, wherein said three-dimensional structure is composed of cubic, spatially centered unit cells with lattice points coinciding with said nodes.

10. The acetabular implant according to claim 1, wherein said contact surface extends to substantially a semi-sphere on said bone side, whereas opposite to said bone side is provided a socket for receiving a hip head, wherein at least one parameter of said plastically deformable zone from the set of yield strength, elastic modulus, length-to-thickness ratio of the strut elements and/or theoretical density increases from said bone side to said socket.

11. The acetabular implant according to claim 10, wherein said plastically deformable zone comprises successive concentric layers, wherein said parameter for each successive layer increases as the distance between said bone side and the said each successive layer increases.

12. The acetabular implant according to claim 1, wherein at least said plastically deformable zone is produced by an additive manufacturing technique.

13. An acetabular implant to be placed in a hip socket having a bone surface, the acetabular implant having a bone side with a contact surface to be fixed against the bone surface of the hip socket, wherein a plastically deformable zone with an open porous structure connects to said contact surface, said zone being formed by a three-dimensional structure composed of strut elements with opposite ends, wherein these strut elements are connected at their ends in nodes, such that at least three strut elements are connected in each node, wherein said strut elements of said zone are made of a material having an elongation at break of at least 15%, wherein said strut elements have a length between 3 mm and 10 mm.

14. A method for placing the acetabular implant of claim 13 in the patient's hip socket, wherein the acetabular implant is provided which is oversized for said hip socket having a bone surface, wherein the oversized acetabular implant has a bone side with a contact surface which is to be fixed to the bone surface of the hip socket as well as a plastically deformable zone with an open porous structure adjoining said contact surface, wherein said implant is pressed, according to a selected insertion direction, with said contact surface against an inner surface of the hip socket, so that said plastically deformable zone is at least partially deformed and adapted to the shape of the bone surface of the hip socket.

15. The method according to claim 14, wherein a position and an orientation for said acetabular implant in relation to the hip socket are selected, wherein said oversized acetabular implant is subsequently pressed in the hip socket until said position and orientation or a planned deviation from this position and orientation are reached.

16. The method according to claim 14, wherein said acetabular implant is placed in the hip socket by hammering so as to generate a force on said deformable zone resulting in local stresses which are greater than a yield strength of the material from which the deformable zone is made.

17. The method according to claim 14, wherein said acetabular implant is pressed in the hip socket according to said insertion direction and wherein said plastically deformable zone is allowed to penetrate into bone defects present in the hip socket through deformation of the plastically deformable zone.

18. The method according to claim 14, wherein, when said acetabular implant is placed in the hip socket, a plastic deformation of a volume of said plastically deformable zone is applied which amounts to at least 5%.

19. An acetabular implant to be placed in a hip socket having a bone surface, the acetabular implant having a bone side with a contact surface to be fixed against the bone surface of the hip socket, wherein a plastically deformable zone with an open porous structure connects to said contact surface, said zone being formed by a three-dimensional structure composed of strut elements with opposite ends, wherein these strut elements are connected at their ends in nodes, such that at least three strut elements are connected in each node, wherein said strut elements of said zone are made of a material having an elongation at break of at least 15%, wherein said zone has a yield strength comprised between a minimum value and a maximum value, wherein said minimum value corresponds to a maximum load of said zone in vivo, after attaching the implant to the bone surface of the hip socket, and wherein said maximum value corresponds to a medically justifiable maximum load exerted on said bone surface when placing the implant against the bone, and wherein said maximum value of the yield strength of said zone amounts to 1 MPa.

* * * * *